(12) United States Patent
Dekleva et al.

(10) Patent No.: US 12,164,688 B2
(45) Date of Patent: Dec. 10, 2024

(54) SYSTEMS AND METHODS OF TRANSIENT-BASED DECODING OF NEURAL SIGNALS

(71) Applicant: University of Pittsburgh—Of the Commonwealth System of Higher Education, Pittsburgh, PA (US)

(72) Inventors: Brian Dekleva, Pittsburgh, PA (US); Jennifer Lynn Collinger, Pittsburgh, PA (US)

(73) Assignee: University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 0 days.

(21) Appl. No.: 17/939,893

(22) Filed: Sep. 7, 2022

(65) Prior Publication Data

US 2023/0074730 A1    Mar. 9, 2023

Related U.S. Application Data

(60) Provisional application No. 63/242,289, filed on Sep. 9, 2021.

(51) Int. Cl.
*G06F 3/01*           (2006.01)
*A61B 5/372*        (2021.01)
*G06F 3/0484*      (2022.01)

(52) U.S. Cl.
CPC ............ *G06F 3/015* (2013.01); *A61B 5/372* (2021.01); *G06F 3/0484* (2013.01)

(58) Field of Classification Search
CPC ........ G06F 3/015; G06F 3/0484; A61B 5/372
See application file for complete search history.

(56) References Cited

U.S. PATENT DOCUMENTS

| | | | | |
|---|---|---|---|---|
| 7,826,894 B2* | 11/2010 | Musallam | ............... | G06F 3/015 600/545 |
| 10,779,746 B2* | 9/2020 | Even-Chen | .......... | A61B 5/7267 |
| 11,752,349 B2* | 9/2023 | Schwemmer | ........... | G06F 3/015 607/48 |
| 2017/0172497 A1* | 6/2017 | Marquez Chin | ..... | A61B 5/7246 |

(Continued)

OTHER PUBLICATIONS

Dekleva, et al., "Generalizable Cursor Click Decoding Using Grasp-Related Neural Transients," *Journ. of Neural Engineering*, vol. 18, 13 pages (Aug. 2021).

*Primary Examiner* — Bryan Earles
(74) *Attorney, Agent, or Firm* — Foley & Lardner LLP (57) ABSTRACT

Disclosed herein are methods and systems for transient-based decoding of neural signals. In one aspect, a device such as a brain-computer interface (BCI), includes at least one processor configured to receive a plurality of neural signals from a subject. The at least one processor can detect, from the plurality of neural signals, first neural activity unique to a first defined temporal window corresponding to an onset phase of an intended action of the subject. The at least one processor can detect, from the plurality of neural signals, second neural activity unique to a second defined temporal window, occurring after the first temporal window and corresponding to an offset phase of the intended action. The at least one processor can generate at least one output indicative of the intended action, responsive to detecting at least one of the first neural activity or the second neural activity.

20 Claims, 6 Drawing Sheets

(56) References Cited

U.S. PATENT DOCUMENTS

| | | | |
|---|---|---|---|
| 2017/0285756 A1* | 10/2017 | Wang | G06F 3/0346 |
| 2020/0275895 A1* | 9/2020 | Barachant | A61B 5/6831 |
| 2021/0106830 A1* | 4/2021 | Provenza | A61B 5/316 |
| 2021/0142214 A1* | 5/2021 | Maalouf | A61B 5/02416 |
| 2021/0251555 A1* | 8/2021 | Darvishi | A61B 5/378 |
| 2023/0253104 A1* | 8/2023 | Serruya | A61N 1/36003 623/25 |

* cited by examiner

Receive a plurality of neural signals from a subject
310

Detect, from the plurality of neural signals, first neural activity within a first defined temporal window corresponding to an onset phase of an intended action of the subject
320

Detect, from the plurality of neural signals, second neural activity within a second defined temporal window, occurring after the first temporal window and corresponding to an offset phase of the intended action
330

Generate at least one output indicative of the intended action, responsive to detecting at least one of the first neural activity or the second neural activity
340

SYSTEMS AND METHODS OF TRANSIENT-BASED DECODING OF NEURAL SIGNALS

CROSS-REFERENCE TO RELATED APPLICATION

This application is related to and claims priority under 35 U.S. § 119(e) from U.S. Provisional Application No. 63/242,289, filed Sep. 9, 2021, titled "SYSTEMS AND METHODS OF TRANSIENT-BASED DECODING OF NEURAL SIGNALS," the entire contents of which are incorporated herein by reference for all purposes.

STATEMENT OF GOVERNMENT SUPPORT

This invention was made with government support under NS107714 and NS108922 awarded by the National Institutes of Health, and N66001-16-C-4051 awarded by the Defense Advanced Research Projects Agency (DARPA) & Space and Naval Warfare Systems Center Pacific (SSC Pacific). The government has certain rights in the invention.

FIELD OF DISCLOSURE

The present disclosure is generally related to use of neural signals, including but not limited to devices, systems and methods of transient-based decoding of neural signals.

BACKGROUND

The loss of (e.g., upper limb) motor function due to injury or disease affects the ability to perform physical activities of daily living, including operating electronic devices. Brain-computer interface (BCI) technology may provide device (e.g., cursor) control for use with computer-based applications. Device control that enables computer use can provide a means of connecting to the world, and can greatly improve quality of life for those living with severe motor impairment by allowing access to web browsing, social media, electronic games, or text-based communication.

SUMMARY

In one aspect, encompassed by the disclosure is a device for processing neural signals, including at least one processor configured to receive a plurality of neural signals from a subject. The at least one processor can detect, from the plurality of neural signals, first neural activity unique to a first defined temporal window corresponding to an onset phase of an intended action of the subject. The at least one processor can detect, from the plurality of neural signals, second neural activity unique to a second defined temporal window, occurring after the first temporal window and corresponding to an offset phase of the intended action. The at least one processor can generate at least one output indicative of the intended action, responsive to detecting at least one of the first neural activity or the second neural activity.

In some embodiments, the at least one processor is configured to at least one of: detect the onset phase by detecting that a probability of a presence of the first neural activity corresponding to the onset phase is at least one of greater than a first defined value, or greater than a probability of a presence of the second neural activity corresponding to the offset phase, or detect the offset phase by detecting that the probability of the presence of the second neural activity corresponding to the offset phase is at least one of greater than a second defined value, or greater than the probability of the presence of the first neural activity corresponding to the onset phase.

In some embodiments, the at least one processor is further configured to reduce the plurality of neural signals to a first subset of neural signals and a second subset of neural signals. The at least one processor can detect, using the first subset of neural signals, the first neural activity, and can detect, using the second subset of neural signals, the second neural activity. In some embodiments, the at least one processor is further configured to perform reduction of the plurality of neural signals using another plurality of neural signals different from the plurality of neural signals.

In some embodiments, the at least one processor is further configured to at least one of shift the first temporal window over time to isolate the first neural activity, or shift the second temporal window over time to isolate the second neural activity.

In some embodiments, the onset phase of the intended action corresponds to one of a grasp, click, pull, activate, press, push or application of force or pressure. The offset phase of the intended action may correspond to one of an ungrasp, release, relaxation, unclick, or termination of the force or pressure. In some embodiments, the intended action corresponds to a grasp and ungrasp action, a click and release action, an activate and release action, a press and release action, a drag and drop action, a pull and release action, or an application of force or pressure sustained over a finite period.

The disclosure further encompasses, in some aspects, a method of using or operating a device such as a BCI, that includes receiving a plurality of neural signals from a subject. The method may include detecting, from the plurality of neural signals, first neural activity unique to a first defined temporal window corresponding to an onset phase of an intended action of the subject. The method may include detecting, from the plurality of neural signals, second neural activity unique to a second defined temporal window, occurring after the first temporal window and corresponding to an offset phase of the intended action. The method may include generating at least one output indicative of the intended action, responsive to detecting at least one of the first neural activity or the second neural activity.

In some embodiments, the method includes at least one of: detecting the onset phase by detecting that a probability of a presence of the first neural activity corresponding to the onset phase is at least one of greater than a first defined value, or greater than a probability of a presence of the second neural activity corresponding to the offset phase, or detecting the offset phase by detecting that the probability of the presence of the second neural activity corresponding to the offset phase is at least one of greater than a second defined value, or greater than the probability of the presence of the first neural activity corresponding to the onset phase.

In some embodiments, the method includes reducing the plurality of neural signals to a first subset of neural signals and a second subset of neural signals. The method may include detecting, using the first subset of neural signals, the first neural activity, and detect, using the second subset of neural signals, the second neural activity. In some embodiments, the method includes training a model to perform reduction of the plurality of neural signals using another plurality of neural signals different from the plurality of neural signals.

In some embodiments, the method includes at least one of: shifting the first temporal window over time to isolate the first neural activity, or shifting the second temporal window over time to isolate the second neural activity.

The disclosure further encompasses, in some aspects, a non-transitory computer-readable medium storing a program including instructions that, when executed by at least one processor, causes the at least one processor to receive a plurality of neural signals from a subject. The processor may detect, from the plurality of neural signals, first neural activity unique to a first defined temporal window corresponding to an onset phase of an intended action of the subject. The at least one processor may detect, from the plurality of neural signals, second neural activity unique to a second defined temporal window, occurring after the first temporal window and corresponding to an offset phase of the intended action. The at least one processor may generate at least one output indicative of the intended action, responsive to detecting at least one of the first neural activity or the second neural activity.

In some embodiments, the instructions that, when executed by the at least one processor, cause the at least one processor to at least one of: detect the onset phase by detecting that a probability of a presence of the first neural activity corresponding to the onset phase is at least one of greater than a first defined value, or greater than a probability of a presence of the second neural activity corresponding to the offset phase, or detect the offset phase by detecting that the probability of the presence of the second neural activity corresponding to the offset phase is at least one of greater than a second defined value, or greater than the probability of the presence of the first neural activity corresponding to the onset phase.

In some embodiments, the instructions that, when executed by the at least one processor, cause the at least one processor to reduce the plurality of neural signals to a first subset of neural signals and a second subset of neural signals. The at least one processor may detect, using the first subset of neural signals, the first neural activity, and detect, using the second subset of neural signals, the second neural activity. In some embodiments, the instructions that, when executed by the at least one processor, cause the at least one processor to train a model to perform reduction of the plurality of neural signals using another plurality of neural signals different from the plurality of neural signals.

In some embodiments, the instructions that, when executed by the at least one processor, cause the at least one processor to at least one of: shift the first temporal window over time to isolate the first neural activity, or shift the second temporal window over time to isolate the second neural activity.

The disclosure further encompasses, in some aspects, a method for training motor function in a subject in need, including implementing any embodiment of brain-computer interface (BCI) in the present disclosure, or using a BCI according to any method in the present disclosure, in the subject. The disclosure further encompasses, in some aspects, a method for rehabilitation in a subject in need, including implementing any embodiment of BCI in the present disclosure, or using a BCI according to any method in the present disclosure, in the subject.

The disclosure further encompasses, in some aspects, a method for treatment of brain related disease, injury or disorder in a subject in need, including implementing any embodiment of BCI in the present disclosure, or using BCI according to any method in the present disclosure, in the subject. The disclosure further encompasses, in some aspects, a method for detection or diagnosis of brain damage, brain function disorder or brain injury in a subject in need, including implementing any embodiment of BCI in the present disclosure, or using a BCI according to any method in the present disclosure, in the subject.

The disclosure further encompasses, in some aspects, a method for control of an assistive device of a subject, including implementing any embodiment of BCI in the present disclosure, or using a BCI according to any method in the present disclosure, in the subject.

Both the foregoing summary and the following description of the drawings and detailed description are exemplary and explanatory. They are intended to provide further details of the disclosure, but are not to be construed as limiting. Other objects, advantages, and novel features will be readily apparent to those skilled in the art from the following detailed description of the disclosure.

DETAILED DESCRIPTION

Brain-computer interfaces (BCIs) such as intracortical BCIs (iBCIs) can restore independence for individuals with significant motor or communication impairments. BCIs may be defined herein as devices that enable a user to control an external device using their neural activity. One of the applications for clinical translation of BCI technology is enabling control of an external device such as a computer cursor. In some embodiments, movement-related neural activity is interpreted (e.g., decoded) and can be used to drive an action, activity or function, such as cursor function/control. For example, cursor movement may be controlled, and neural signals may be detected, by having the motor-impaired subject, who may not be able to actually move his or her limbs, imagine performing reaching movement. Described herein are aspects of a system and method to improve cursor click decoding to allow for both point-and-click and click-and-drag control for instance, although the scope and spirit of the disclosure includes any application of using neural signals to control a device.

Some approaches for controlling cursor click function use binary state classification methods to attempt to categorize recorded neural activity as belonging to either an un-grasped (e.g., un-clicked) state or a grasped (e.g., clicked) state. These binary-state approaches are unable to provide reliable click-and-drag control. For example, using the binary-state approach can cause the cursor to be intermittently released during click-and-drag control, such that the subject may have to perform click-and-drag multiple times in order to successfully move an icon or other displayed entity to its intended destination. The restriction of decoding approaches to only discrete click control arises from a difficulty in identifying salient, continuous neural responses that are unique to grasp. In some examples, grasp-related features of neural activity are attenuated during attempted/imagined arm translation.

In accordance with some of the aspects disclosed herein, a system and method for controlling mechanical or electronic function (e.g., cursor click function) using brain (e.g., neural, motor cortical or premotor cortical) activity recorded by a BCI uses a different set of cortical responses to achieve control. Some embodiments of the present system and method detect transient responses from neural activity in the brain (e.g., motor cortex or premotor cortex) at the onset and/or offset of an action (e.g., grasp) intent (e.g., when a subject having motor impairment attempts to make a grasping movement) rather than attempting to identify the grasp state continuously (e.g., maintained over a duration) from the neural activity. Aspects of the present system and method use these transient responses to control the transitions between un-clicked and clicked states, for instance.

This transient-based approach may allow for an improvement in success rate during an operation or task (e.g., click-and-drag task) over the alternative binary state approach. Some embodiments of the transient-based approach can increase signal-to-noise ratio and can improve reliability. By controlling click state transitions, some potential detection error types may have no deleterious effect on performance. For example, detection of an onset transient response may have no effect when the cursor is already in the clicked state. A transient-based approach for identifying hand grasp can, for example, provide a high degree of cursor click control for both point-and-click and click-and-drag applications. The transient-based approach can, for example, allow a subject to reliably move an icon or other displayed entity to its destination with a single click-and-drag.

Figure 1:
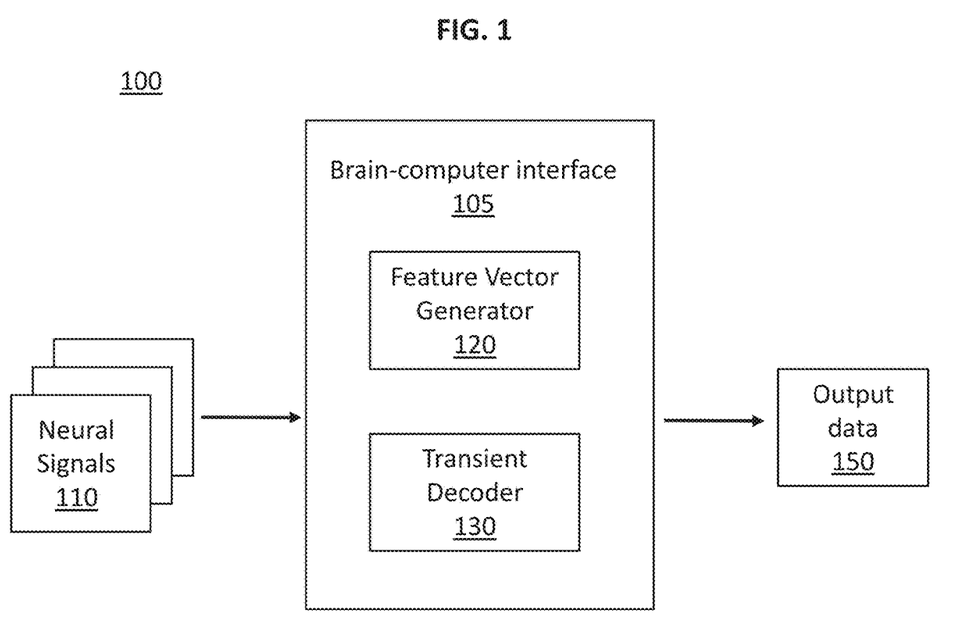
FIG. 1 is a block diagram of a system for use with a method described herein, according to one or more disclosed embodiments.

In certain embodiments, disclosed herein is a system (or device) for use with one or more of the methods described herein. FIG. 1 is a block diagram of a system 100 for decoding neural signals, according to an example implementation of the present disclosure. The system 100 can include a device for processing neural signals, such as a brain-computer interface 105 which can further include a feature vector generator 120 and/or a transient decoder 130. One or more of these components may operate together to receive a number of neural signals 110 from a subject and can subsequently provide output data 150 to an external device to the subject. Each of the components disclosed herein is implemented on a hardware, or a combination of software and hardware. For example, one or more of the components can be implemented as software modules executing on one or more processors. For another example, one or more of the components can be implemented as/in one or more hardware components such as a neural network chip, a field programmable gate logic (FPGA) and/or an application specific integrated circuit (ASIC). In some embodiments, the system 100 includes more, fewer, or different components than shown in FIG. 1.

In some embodiments, the feature vector generator 120 includes or corresponds to a component that receives neural signals 110 over a period of time. The period of time may encompass neural activity indicating an onset of an intended action (e.g., click) and neural activity indicating an offset of the action (e.g., release). An intended action may comprise a planned, meant, deliberate, intentional, calculated and/or conscious action, or an action that is willed, caused, triggered and/or controlled by a subject's thought(s), neural activity or mental state. Each of the neural signals 110 may refer to a signal detected in the brain (e.g., change in the voltage across a neuron membrane due to the flow of ions into and out of the neuron), or any information (e.g., estimated firing or spike rates) derived from the detected signal in the brain. In some instances, the feature vector generator 120 receives the neural signals 110 from an implanted or wearable detector/measurement device on a subject. The implanted device may be implanted in a brain (e.g., motor cortex or premotor cortex) of the subject. The implanted device may include microelectrode arrays. In some implementations, the neural signals 110 received from the implanted device are filtered using one or more filters (e.g., a $4^{th}$ order 250 Hz high pass filter and/or a 440 ms decaying exponential filter).

The feature vector generator 120 can identify patterns (e.g., a grouping/cluster, timing, temporal relationship, and/or intensity) of neural activity by searching, processing, and/or analyzing the neural signals 110 and/or neural activity associated with the neural signals 110. The feature vector generator 120 can shift/sweep/scan one or more temporal windows across the period of time. Each temporal window (e.g., window or frame of time) can have, or be associated with, a window start time and a window end time, and/or a window width, which may be defined as an absolute difference of the window start time and the window end time. In each temporal window, the feature vector generator 120 can search for unique neural activity.

In some aspects, each temporal window of neural activity includes a feature vector that is arranged in a multi-dimensional space. Each dimension may correspond to a different feature of the feature vector. In some embodiments, the feature vector generator 120 calculates a weight for each of the features. In some implementations, using the weights, the feature vector generator 120 reduces the multi-dimensional space to a reduced multi-dimensional space with less dimensions than the multi-dimensional space. For example, the feature vector generator 120 can apply factor analysis (FA) or principal component analysis (PCA) to the weights to perform dimensionality reduction. In some implementations, the feature vector generator 120 does not reduce the dimensionality of the space, but instead reorganizes (e.g. rotates) to a new multi-dimensional space of the same dimensionality.

In some embodiments, the feature vector generator 120 classifies each temporal window of neural activity. Specifically, in some implementations, the feature vector generator 120 fits a classifier (e.g., a linear classifier such as a linear discriminant classifier (LDA) or a hidden Markov model (HMM)) on the neural activity. In some embodiments, the feature vector generator 120 uses the classifier to generate a classifier output/binary decision (e.g., class A if neural activity occurs in window, class B otherwise) for each type of neural activity (e.g., click, release, etc.) and each temporal window of neural activity that indicates whether there is isolated neural activity in the given window (e.g., there is a difference greater than a predetermined threshold in the neural activity of the given window and the adjacent windows). In some embodiments, the classifier output is provided into a correlator that determines a probability associated with each binary classification. Examples of the correlator include a Matthews Correlation Coefficient (MCC) and an adjusted version of MCC. In some aspects, the correlator measures/indicates classification performance of the classifier, as explained further below.

Figure 2:
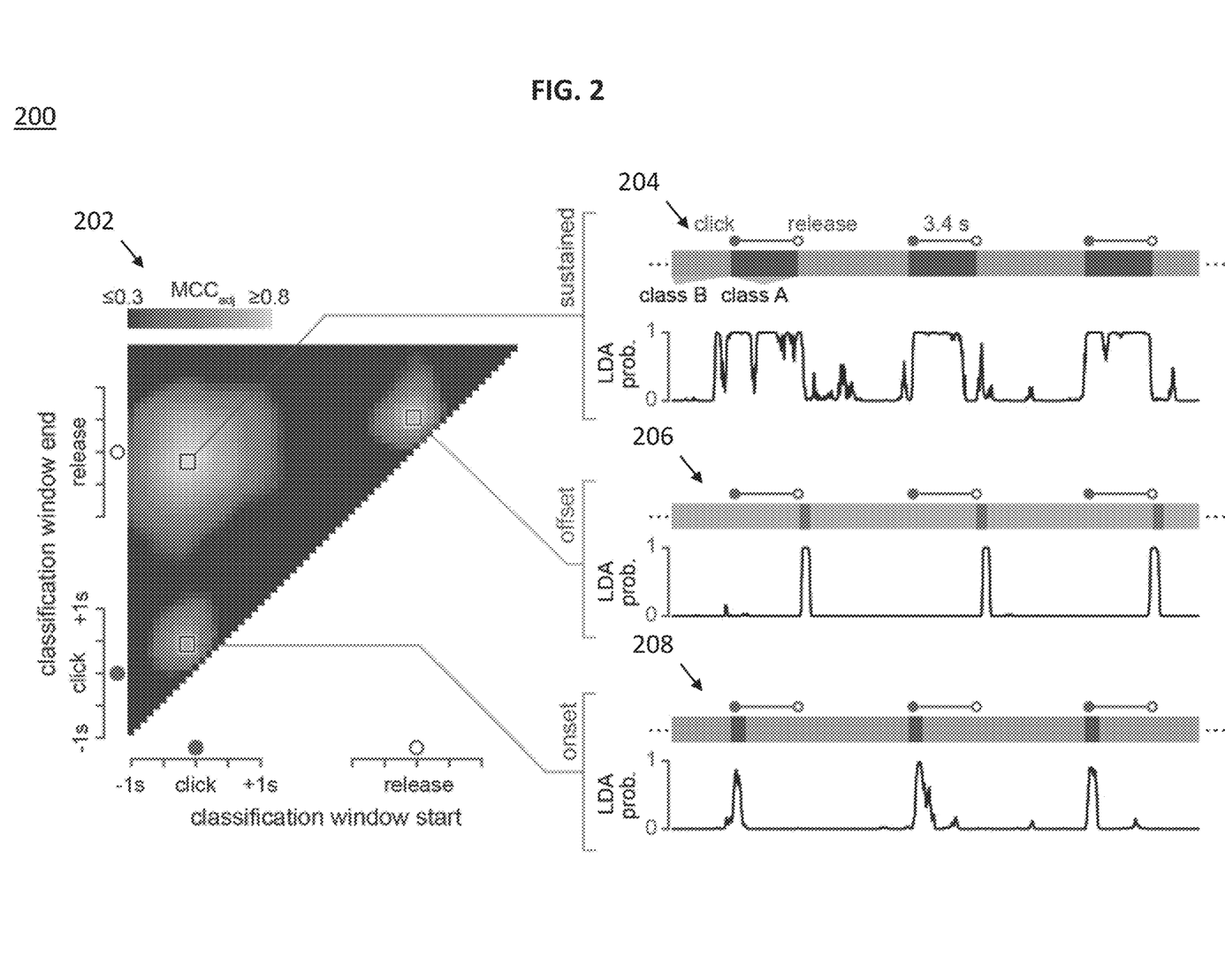
FIG. 2 illustrates an example performance summary of a classifier, in accordance with some embodiments of the disclosure.

FIG. 2 illustrates an example performance summary 200 of a classifier, in accordance with some embodiments of the disclosure. Graph 202 shows discriminability of neural activity (e.g., neural activity that occurs in the given window but not in the neighboring windows) in various temporal windows around an action such as a click and release action. The x-axis represents the classification window start and the y-axis represents the classification window stop/end. Thus, each point in the graph 202 represents a temporal window relative to click/release, which was used to assigned class labels to the neural data. The window width of each point is determined as the y-axis value of the point less than the x-axis value of the point. The color/contrast/intensity at each point can represent the performance (e.g., using adjusted Matthews Correlation Coefficient; MCCadj) achieved by an LDA classifier in isolating neural activity from within the given window. In some embodiments, graph 202 shows offline or calibration activity. Graph 202 can be used to select a window width and start time. A window width can be selected that can increase the discriminability of the appropriate response type. For example, a narrower window width can be selected for an offset transient and/or an onset transient.

Graphs 204-208 show example classification probability traces from three local maxima identified through this grid search process: sustained response (graph 204), offset transient (graph 206), and onset transient (graph 208). The x-axis represents time and the y-axis represents the probability that the activity belongs to the associated window. In some embodiments, graphs 204-208 show offline reconstructions of classification probabilities (LDA). Each classifier identifies activity unique to a given window associated with click and/or release action, these windows using the respective widths and temporal offsets selected based on the graph 202.

In some embodiments, the feature vector generator 120 is applied offline to neural activity (e.g., where stored or previously obtained neural activity can be accessed for use) that is used for training/calibrating the decoder ("training neural activity"). In some aspects, the correlator measures/indicates classification performance of the classifier. In some implementations, multiple classifiers are applied to the neural activity to determine a classifier with a highest classification performance. In some implementations, different classifiers are used for different types of neural activity. For example, one classifier may be trained to identify a neural activity pattern associated with the onset of the intended action and another may be trained to identify a neural activity pattern associated with the offset (an opposing or counterbalancing phase/state/transition to the onset) of the intended action.

In some aspects, the feature vector generator 120 determines (a) a window start time, or a range of window start times, relative to a reference time, and/or (b) a window width/size, or a range of window widths/sizes, of the temporal window which is most likely to correspond to each type of neural activity.

In some implementations, the feature vector generator 120 determines (e.g., calibrates, extracts, etc.) a time difference between a time of the neural activity and a time of a physical action of the subject which corresponds to the intended action. In some embodiments, during the offline phase, a time of the actual physical action (e.g., the application of isometric force or wrist rotation) is measured in parallel with the neural activity. From this, the time difference can be extracted.

In some embodiments, the feature vector generator 120 is applied online during run-time to neural activity that is used to control intended actions ("run-time neural activity"), which is further explained below. During run-time, the classifier(s), trained using the window offset(s), the window width(s) and/or the time difference selected during offline calibration, are applied to the run-time neural activity.

The transient decoder 130 can convert the classifier outputs of the feature vector generator 120 to (e.g., generate) output data 150. Output data 150 may include, by way of a non-limiting illustration, a click state associated with each temporal window (e.g., time range) for a certain window width. The click state may include a clicked state and an unclicked state. Output data 150 may include a first signal interpreted by an external device as an onset of a clicked state and a second signal interpreted by an external device as an offset of the clicked state.

As mentioned before, each classifier output may be associated with a probability. In some embodiments, a heuristic can be used to convert a classifier output to a click function. For example, if the cursor is in the unclicked state and the probability of an onset transition is greater than (a) a predetermined threshold (e.g., 0.2), (b) a probability of an offset transition, or (c) both, the transient decoder 130 determines that the cursor has transitioned to the clicked state. Likewise, in some aspects, if the cursor is in the clicked state, and the probability of an offset transition is greater than (a) a predetermined threshold (e.g., 0.2), (b) a probability of an onset transition, or (c) both, the transient decoder 130 can determine that the cursor has transitioned to the unclicked state.

In some embodiments, the transient decoder 130 includes or corresponds to a component that provides output data 150 to an external device. The external device may include a mouse, a keyboard, a monitor, a computer, a mobile device, an Internet of things (IoT) device, a robot, an exoskeleton, a neuromodulatory device, a prosthetic, computer-assisted, and/or robotic limb or other body part, and the like.

Figure 3:
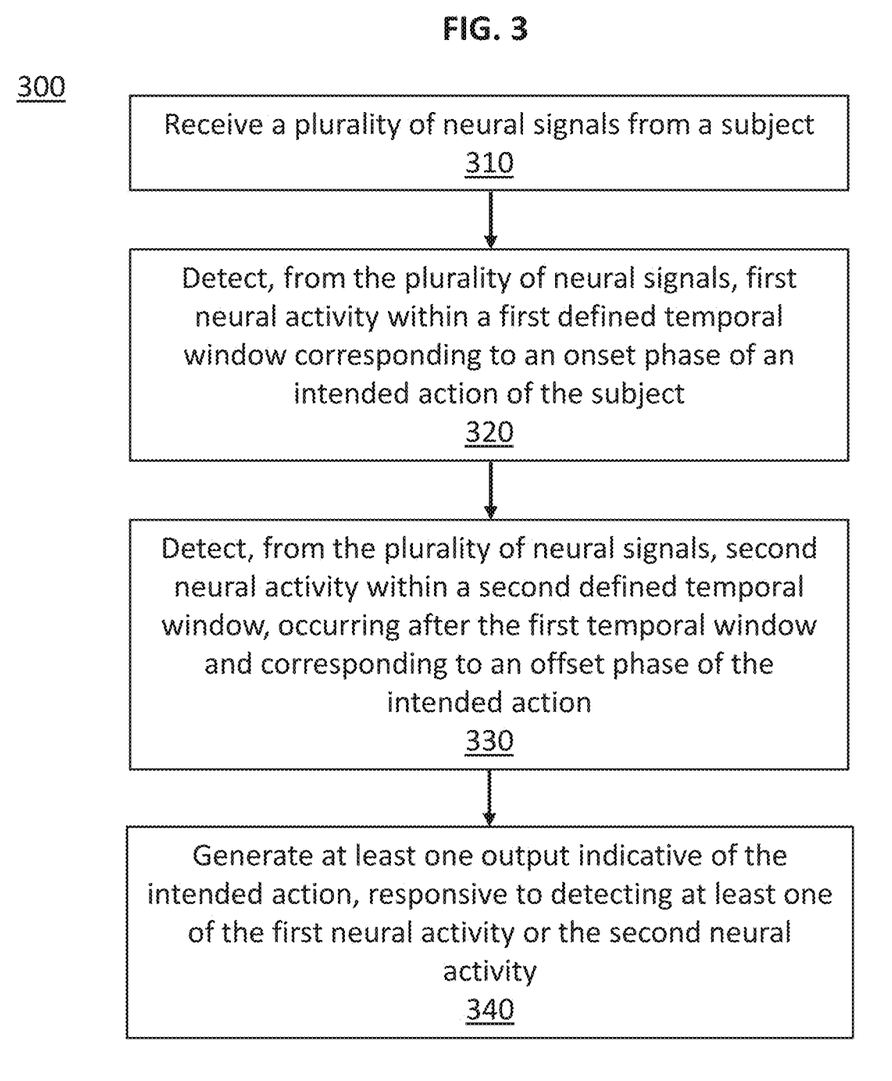
FIG. 3 is a flow chart illustrating a method of transient-based decoding of neural signals, according to one or more disclosed embodiments.

FIG. 3 is a flow chart illustrating a method 300 of transient-based decoding of neural signals, according to one or more disclosed embodiments. The method 300 is performed by the system 100, or a device such as the brain-computer interface 105, or one or more processors associated with the system 100 and/or the device. In some embodiments, the system 100 or the device is implemented by a single system. In other embodiments, the system 100 or the device (e.g., brain-computer interface 105) is implemented by separate systems. In some embodiments, the method 300 includes more, fewer, or different steps than shown in FIG. 3.

In one approach, the device, such as a brain-computer interface 105, performs a number of steps or operations. By way of an example, the brain-computer interface 105 receives a plurality of neural signals from a subject (310), detects, from the plurality of neural signals, first neural activity unique to (e.g., characteristic of, correlated to), or otherwise within or corresponding to, a first defined (e.g., predefined or configured during calibration or runtime) temporal window corresponding to an onset phase of an intended action of the subject (320), detects, from the plurality of neural signals, second neural activity unique to a second defined temporal window, occurring after the first temporal window and corresponding to an offset phase of the intended action (330), and/or generates at least one output (e.g., a signal, an instruction, a mechanical/physical action/motion, an audio output, a visual output on a display for instance) indicative of the intended action, responsive to detecting at least one of the first neural activity or the second neural activity (340).

In further detail of 310, and in some embodiments, the brain-computer interface 105 receives a plurality of neural signals (neural signals 110) from a subject. In some embodiments, the brain-computer interface 105 receives the neural signals from an implanted or wearable detector/measurement device on a subject. The implanted device may be implanted in a motor cortex of the subject. The implanted device may include microelectrode arrays.

In further detail of 320, and in some embodiments, the brain-computer interface 105 detects, from the plurality of neural signals, first neural activity unique to a first defined temporal window corresponding to an onset phase of an intended action of the subject. In some embodiments, the onset phase of the intended action corresponds to one of a grasp, click, pull, activate, press, push or application of force or pressure. In some embodiments, the brain-computer interface 105 detects the onset phase by detecting that a probability of a presence of the first neural activity corresponding to the onset phase is at least one of greater than a first defined value (e.g., 0.5 or 50%; or 0.6 or 60%; or 0.7 or 70%; or 0.8 or 80%; or 0.9 or 90%), or greater than a probability of a presence of the second neural activity corresponding to the offset phase. In some embodiments, the brain-computer interface 105 identifies the appropriate temporal window for calibration (e.g. classifier training) by comparing or matching portions of neural activity against a defined/predicted/projected pattern or features of neural activity, and/or determining the extent or probability of a match with the pattern or features.

In some embodiments, the intended action corresponds to a grasp and ungrasp action, a click and release action, an activate and release action, a press and release action, a drag and drop action, a pull and release action, or an application of force or pressure sustained over a finite period. In some embodiments, click decoding can be combined with other methods of control (e.g., other methods of decoding of cursor position, such as sustained decoding, from the BCI or some other input device).

In further detail of 330, and in some embodiments, the brain-computer interface 105 detects, from the plurality of neural signals, second neural activity unique to a second defined temporal window, occurring after the first temporal window and corresponding to an offset phase of the intended action. In some embodiments, the offset phase of the intended action corresponds to one of an ungrasp, release, relaxation, unclick, or termination of the force or pressure. In some embodiments, the brain-computer interface 105 detects the offset phase by detecting that the probability of the presence of the second neural activity corresponding to the offset phase is at least one of greater than a second defined value (e.g., 0.5 or 50%; or 0.6 or 60%; or 0.7 or 70%; or 0.8 or 80%; or 0.9 or 90%), or greater than the probability of the presence of the first neural activity corresponding to the onset phase. In some embodiments, the brain-computer interface 105 identifies the appropriate temporal window for calibration (e.g. classifier training) by comparing or matching portions of neural activity against another defined/predicted/projected pattern or features of neural activity, and/or determining the extent or probability of a match with the another pattern or features.

In some embodiments, the brain-computer interface 105 reduces (e.g., filters, processes, transforms) the plurality of neural signals to a first subset of neural signals and a second subset of neural signals. In some embodiments, the brain-computer interface 105 reduces the plurality of neural signals using some implementation (e.g., offline or online) of factor analysis (FA) or principal component analysis (PCA). In some embodiments, the brain-computer interface 105 detects, using the first subset of neural signals, the first neural activity. In some embodiments, the brain-computer interface 105 detects, using the second subset of neural signals, the second neural activity.

In some embodiments, the brain-computer interface 105 trains a model (e.g., classifier, correlator), or the brain-computer interface 105 is trained, to perform classification and/or reduction of the plurality of neural signals using another plurality of neural signals different from the plurality of neural signals. The other plurality of neural signals may be neural signals received and analyzed during a calibration/offline/training (or non-runtime) phase. For example, the model (e.g., classifier, correlator) or the brain-computer interface 105 may be trained to generate, predict, project, detect, identify and/or recognize one or more patterns or features of neural activity unique to a time window, that can correspond to features of an intended action, such as an onset phase and/or offset phase of the intended action.

In further detail of 340, and in some embodiments, the brain-computer interface 105 generates at least one output (e.g., output data 150) indicative of the intended action, responsive to detecting at least one of the first neural activity or the second neural activity. In some embodiments, the brain-computer interface 105 provides the output to an external device. The output may include one of a clicked state and an unclicked state associated with each temporal window (e.g., time range) for a certain/defined/predetermined window width. The output may include a first signal interpreted by an external device as an onset of a clicked state and a second signal interpreted by an external device as an offset of the clicked state.

In some embodiments, a method for one or more of (a) training motor function in a subject in need, (b) rehabilitation in a subject in need (c) treatment of brain related disease, injury or disorder in a subject in need (d) detection or diagnosis of brain damage, brain function disorder or brain injury in a subject in need, (e) control of an assistive device of a subject (e.g., in a subject in need) can use the brain-computer interface 105 according to one or more of the steps or embodiments of method 300. In some embodiments, the assistive device includes a robot, a remote-controlled device, an exoskeleton, a neuromodulatory device, and/or a computer. One application of the present system or method is to emulate mouse, controller, joystick, trigger, keyboard or other device actions.

Figure 4:
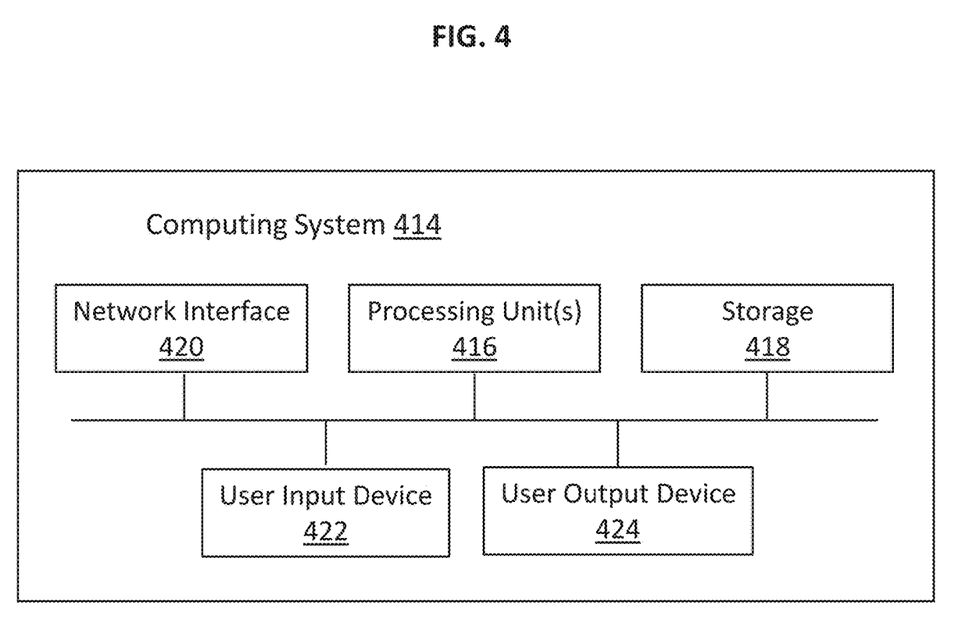
FIG. 4 is a block diagram of a computing environment according to an example implementation of the present disclosure.

Various operations described herein can be implemented on one or more computer systems. FIG. 4 shows a block diagram of a representative computing system 414 usable to implement the present disclosure. In some embodiments, the system 100, the device or the brain-computer interface 105 is implemented by the computing system 414. Computing system 414 can be implemented, for example, as a consumer device such as a smartphone, other mobile phone, tablet computer, wearable computing device (e.g., smart watch, eyeglasses, head mounted display), desktop computer, laptop computer, cloud computing service or implemented with distributed computing devices. In some embodiments, the computing system 414 can include computer components such as processors 416, storage device 418, network interface 420, user input device 422, and user output device 424.

Network interface 420 can provide a connection to a wide area network (e.g., the Internet) to which WAN interface of a remote server system is also connected. Network interface 420 can include a wired interface (e.g., Ethernet) and/or a wireless interface implementing various RF data communication standards such as Wi-Fi, Bluetooth, or cellular data network standards (e.g., 3G, 4G, 5G, 60 GHz, LTE, etc.).

User input device 422 can include any device (or devices) via which a user can provide signals to computing system 414; computing system 414 can interpret the signals as indicative of particular user requests or information. User input device 422 can include any or all of a keyboard, a controller (e.g., joystick), touch pad, touch screen, mouse or other pointing device, scroll wheel, click wheel, dial, button, switch, keypad, microphone, sensors (e.g., a motion sensor, an eye tracking sensor, etc.), and so on.

User output device 424 can include any device via which computing system 414 can provide information to a user. For example, user output device 424 can include a display to display images generated by or delivered to computing system 414. The display can incorporate various image generation technologies, e.g., a liquid crystal display (LCD), light-emitting diode (LED) including organic light-emitting diodes (OLED), projection system, cathode ray tube (CRT), or the like, together with supporting electronics (e.g., digital-to-analog or analog-to-digital converters, signal processors, or the like). A device such as a touchscreen that function as both input and output device can be used. Output devices 424 can be provided in addition to or instead of a display. Examples include indicator lights, speakers, tactile "display" devices, printers, and so on.

Some implementations include electronic components, such as microprocessors, storage and memory that store computer program instructions in a non-transitory computer readable storage medium. Many of the features described in this specification can be implemented as processes that are specified as a set of program instructions encoded on a computer readable storage medium. When these program instructions are executed by one or more processors, they cause the processors to perform various operation indicated in the program instructions. Examples of program instructions or computer code include machine code, such as is produced by a compiler, and files including higher-level code that are executed by a computer, an electronic component, or a microprocessor using an interpreter. Through suitable programming, processor 416 can provide various functionality for computing system 414, including any of the functionality described herein as being performed by a server or client, or other functionality associated with message management services.

It will be appreciated that computing system 414 is illustrative and that variations and modifications are possible. Computer systems used in connection with the present disclosure can have other capabilities not specifically described here. Further, while computing system 414 is described with reference to particular blocks, it is to be understood that these blocks are defined for convenience of description and are not intended to imply a particular physical arrangement of component parts. For instance, different blocks can be located in the same facility, in the same server rack, or on the same motherboard. Further, the blocks need not correspond to physically distinct components. Blocks can be configured to perform various operations, e.g., by programming a processor or providing appropriate control circuitry, and various blocks might or might not be reconfigurable depending on how the initial configuration is obtained. Implementations of the present disclosure can be realized in a variety of apparatus including electronic devices implemented using any combination of circuitry and software.

Having now described some illustrative implementations, it is apparent that the foregoing is illustrative and not limiting, having been presented by way of example. In particular, although many of the examples presented herein involve specific combinations of method acts or system elements, those acts and those elements can be combined in other ways to accomplish the same objectives. Acts, elements and features discussed in connection with one implementation are not intended to be excluded from a similar role in other implementations or implementations.

The hardware and data processing components used to implement the various processes, operations, illustrative logics, logical blocks, modules and circuits described in connection with the embodiments disclosed herein may be implemented or performed with a general purpose single- or multi-chip processor, a digital signal processor (DSP), an application specific integrated circuit (ASIC), a field programmable gate array (FPGA), or other programmable logic device, discrete gate or transistor logic, discrete hardware components, or any combination thereof designed to perform the functions described herein. A general purpose processor may be a microprocessor, or, any conventional processor, controller, microcontroller, or state machine. A processor also may be implemented as a combination of computing devices, such as a combination of a DSP and a microprocessor, a plurality of microprocessors, one or more microprocessors in conjunction with a DSP core, or any other such configuration. In some embodiments, particular processes and methods may be performed by circuitry that is specific to a given function. The memory (e.g., memory, memory unit, storage device, etc.) may include one or more devices (e.g., RAM, ROM, Flash memory, hard disk storage, etc.) for storing data and/or computer code for completing or facilitating the various processes, layers and modules described in the present disclosure. The memory may be or include volatile memory or non-volatile memory, and may include database components, object code components, script components, or any other type of information structure for supporting the various activities and information structures described in the present disclosure. According to an embodiment, the memory is communicably connected to the processor via a processing circuit and includes computer code for executing (e.g., by the processing circuit and/or the processor) the one or more processes described herein.

The present disclosure contemplates methods, systems and program products on any machine-readable media for accomplishing various operations. The embodiments of the present disclosure may be implemented using existing computer processors, or by a special purpose computer processor for an appropriate system, incorporated for this or another purpose, or by a hardwired system. Embodiments within the scope of the present disclosure include program products comprising machine-readable media for carrying or having machine-executable instructions or data structures stored thereon. Such machine-readable media can be any available media that can be accessed by a general purpose or special purpose computer or other machine with a processor. By way of example, such machine-readable media can comprise RAM, ROM, EPROM, EEPROM, or other optical disk storage, magnetic disk storage or other magnetic storage devices, or any other medium which can be used to carry or store desired program code in the form of machine-executable instructions or data structures and which can be accessed by a general purpose or special purpose computer or other machine with a processor. Combinations of the above are also included within the scope of machine-readable media. Machine-executable instructions include, for example, instructions and data which cause a general purpose computer, special purpose computer, or special purpose processing machines to perform a certain function or group of functions.

The phraseology and terminology used herein is for the purpose of description and should not be regarded as limiting. The use of "including" "comprising" "having" "containing" "involving" "characterized by" "characterized in that" and variations thereof herein, is meant to encompass the items listed thereafter, equivalents thereof, and additional items, as well as alternate implementations consisting of the items listed thereafter exclusively. In one implementation, the systems and methods described herein consist of one, each combination of more than one, or all of the described elements, acts, or components.

Any references to implementations or elements or acts of the systems and methods herein referred to in the singular can also embrace implementations including a plurality of these elements, and any references in plural to any implementation or element or act herein can also embrace implementations including only a single element. References in the singular or plural form are not intended to limit the presently disclosed systems or methods, their components, acts, or elements to single or plural configurations. References to any act or element being based on any information, act or element can include implementations where the act or element is based at least in part on any information, act, or element.

Any implementation disclosed herein can be combined with any other implementation or embodiment, and references to "an implementation," "some implementations," "one implementation" or the like are not necessarily mutually exclusive and are intended to indicate that a particular feature, structure, or characteristic described in connection with the implementation can be included in at least one implementation or embodiment. Such terms as used herein are not necessarily all referring to the same implementation. Any implementation can be combined with any other implementation, inclusively or exclusively, in any manner consistent with the aspects and implementations disclosed herein.

Where technical features in the drawings, detailed description or any claim are followed by reference signs, the reference signs have been included to increase the intelligibility of the drawings, detailed description, and claims. Accordingly, neither the reference signs nor their absence have any limiting effect on the scope of any claim elements. Technical and scientific terms used herein have the meanings commonly understood by one of ordinary skill in the art, unless otherwise defined. Any suitable materials and/or methodologies known to those of ordinary skill in the art can be utilized in carrying out the methods described herein.

Systems and methods described herein may be embodied in other specific forms without departing from the characteristics thereof. As used herein, "approximately," "about" "substantially" or other terms of degree will be understood by persons of ordinary skill in the art and will vary to some extent on the context in which it is used. If there are uses of the term which are not clear to persons of ordinary skill in the art given the context in which it is used, references to "approximately," "about" "substantially" or other terms of degree shall include variations of +/−10% from the given measurement, unit, or range unless explicitly indicated otherwise.

Coupled elements can be electrically, mechanically, or physically coupled with one another directly or with intervening elements. Scope of the systems and methods described herein is thus indicated by the appended claims, rather than the foregoing description, and changes that come within the meaning and range of equivalency of the claims are embraced therein.

The term "coupled" and variations thereof includes the joining of two members directly or indirectly to one another. Such joining may be stationary (e.g., permanent or fixed) or moveable (e.g., removable or releasable). Such joining may be achieved with the two members coupled directly with or to each other, with the two members coupled with each other using a separate intervening member and any additional intermediate members coupled with one another, or with the two members coupled with each other using an intervening member that is integrally formed as a single unitary body with one of the two members. If "coupled" or variations thereof are modified by an additional term (e.g., directly coupled), the generic definition of "coupled" provided above is modified by the plain language meaning of the additional term (e.g., "directly coupled" means the joining of two members without any separate intervening member), resulting in a narrower definition than the generic definition of "coupled" provided above. Such coupling may be mechanical, electrical, or fluidic.

References to "or" can be construed as inclusive so that any terms described using "or" can indicate any of a single, more than one, and all of the described terms. A reference to "at least one of 'A' and 'B'" can include only 'A', only '13', as well as both 'A' and '13'. Such references used in conjunction with "comprising" or other open terminology can include additional items.

Modifications of described elements and acts such as variations in sizes, dimensions, structures, shapes and proportions of the various elements, values of parameters, mounting arrangements, use of materials, colors, orientations can occur without materially departing from the teachings and advantages of the subject matter disclosed herein. For example, elements shown as integrally formed can be constructed of multiple parts or elements, the position of elements can be reversed or otherwise varied, and the nature or number of discrete elements or positions can be altered or varied. Other substitutions, modifications, changes and omissions can also be made in the design, operating conditions and arrangement of the disclosed elements and operations without departing from the scope of the present disclosure.

References herein to the positions of elements (e.g., "top," "bottom," "above," "below") are merely used to describe the orientation of various elements in the FIGURES. The orientation of various elements may differ according to other exemplary embodiments, and that such variations are intended to be encompassed by the present disclosure.

As used herein, a subject can be a mammal, such as a non-primate (e.g., cows, pigs, horses, cats, dogs, rats, etc.) or a primate (e.g., monkey and human). In certain embodiments, the term "subject," as used herein, refers to a vertebrate, such as a mammal. Mammals include, without limitation, humans, non-human primates, wild animals, feral animals, farm animals, sport animals, and pets. In certain exemplary embodiments, a subject is a human.

As used herein, the terms "subject" and "user" are used interchangeably.

Unless otherwise defined, all technical and scientific terms used herein have the same meaning as commonly understood by one of ordinary skill in the art to which this disclosure belongs. Although methods and materials similar or equivalent to those described herein can be used in the practice or testing of the present disclosure, suitable methods and materials are described herein.

As used herein, the singular forms "a", "an," and "the" include plural referents unless the context clearly indicates otherwise. For example, the term "a cell" includes a plurality of cells, including mixtures thereof.

As used herein, the term "about" is used to indicate that a value includes the standard deviation of error for the device or method being employed to determine the value. The term "about" when used before a numerical designation, e.g., temperature, time, amount, and concentration, including range, indicates approximations which may vary by (+) or (—) 15%, 10%, 5%, 3%, 2%, or 1%.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

EXAMPLES

These examples are provided for illustrative purposes only and not to limit the scope of the claims provided herein.

Example 1—Neural Activity of Motor-Impaired Participants for Cursor Control

Two motor-impaired participants (P2 and P3) were used in a study. P2 is a man with tetraplegia caused by C5 motor/C6 sensory ASIA B spinal cord injury. The participant has some residual upper arm and wrist movement, but no hand function. Approximately five years prior to data collection for the current study, two 88-channel microelectrode arrays (Blackrock Microsystems, Salt Lake City, UT) were implanted in the hand and arm areas of motor cortex. P3 has a C6 ASIA B spinal cord injury. The participant retains some residual arm and wrist movement, but has no hand function. Approximately four months prior to data collection, two 96-channel microelectrode arrays (Blackrock Microsystems, Salt Lake City, UT) were implanted in the hand area of motor cortex. Both participants also had two 64-channel arrays implanted in somatosensory cortex (Flesher et al., 2016), which were not used for this study.

Calibration Tasks

For both participants, we tested two types of calibration routines for translation and click: (1) discrete click center-out, and (2) sustained click center-out. For each session, we selected one calibration type. Decoder calibration occurred at the beginning of the session. During decoder calibration, the participants observed the cursor as it moved under computer control between targets on the screen and transitioned between click states. The participants were asked to perform covert/virtual (e.g., imagined) movements with their right arm corresponding to the cursor translation (e.g. move arm to the left when the cursor moves to the left), and attempted grasp corresponding to cursor click (e.g., grasp for click, release for unclick). Two types of calibration tasks were performed: discrete click calibration task (e.g., the calibration task only included cursor translation while the cursor was in the unclicked state) and sustained click calibration task (e.g., included cursor translation during both clicked and unclicked states).

Decoder Evaluation Tasks

The click decoders were tested to generalize across the two main functions necessary for full click function: point-and-click (discrete click), and click-and-drag. To improve user engagement, the tasks were stylized as helicopter-based arcade games. During each session, the participants first completed sixteen trials of the click-and-drag task with each decoder, followed by sixteen trials of the point-and-click task with each decoder. This sequence then repeated, resulting in thirty-two trials for each decoder/task combination.

In the point-and-click decoder evaluation task, the participant began a trial by moving the unclicked cursor to the center target. An outer target then appeared at one of 8 radial locations and the participant moved the cursor to the target. Once the cursor entered the target, the participant attempted to click and immediately release without leaving the target. A trial was unsuccessful if: a click occurred before reaching the target (early click), the cursor left the target before release (drag out), or the participant remained in any single phase longer than twenty seconds (timeout). In the case of a drag out failure, the cursor was automatically returned to the center target. During the task, early clicks did not trigger immediate trial failure, and the participant could continue to attempt the task. However, trials with early clicks were retroactively judged as failed trials.

In the click-and-drag decoder evaluation task, each trial began when the unclicked cursor entered the center target. An outer target (stylized as a "worried" face) then appeared at one of eight radial locations and the participant was tasked with clicking on the target (cursor overlapping with outer target), dragging it back to the center target (outer target overlapping with center target), and then releasing. A trial was considered unsuccessful if: a click occurred before reaching the target (early click), the dragged target was dropped before returning to the center (drop), or he remained in any single phase longer than twenty seconds (timeout). As in the point-and-click task, early clicks did not trigger immediate trial failure, but were judged as such post-hoc.

Results

Figure 5:
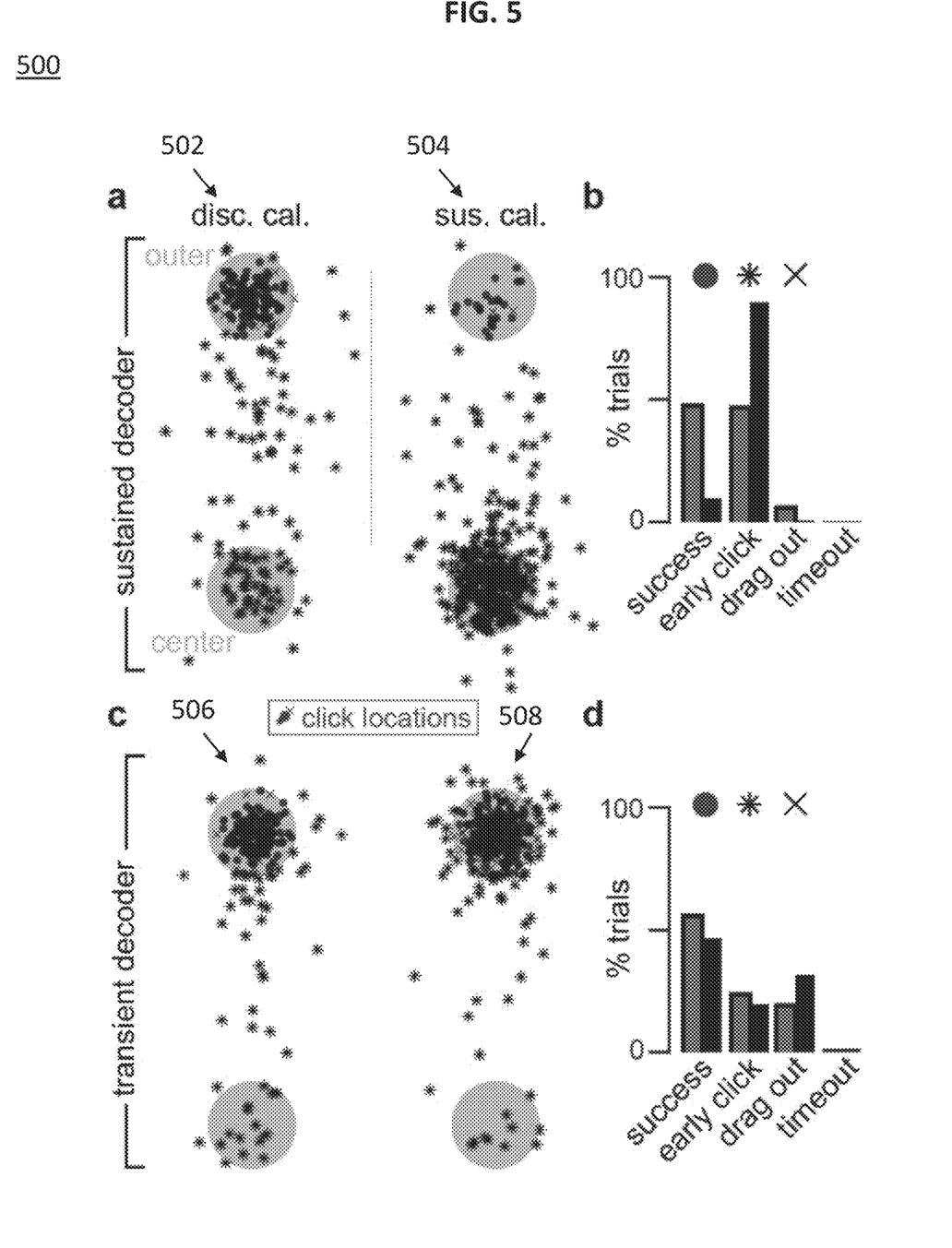
FIG. 5 illustrates results of the point-and-click task, in accordance with some embodiments.

FIG. 5 illustrates results 500 of the point-and-click task, in accordance with some embodiments. Section (a) of FIG. 5 shows click locations (rotated to align across target directions) during sustained decoder trials trained using discrete click calibration (502) or sustained click calibration (504). Dark points or dots represent click locations on successful trials. Star points or asterisks (*) represent the click locations on trials with initial clicks outside of the target. Crosses or 'x's' (x) represent failed trials in which the click occurred inside the target, but the cursor left the target before release. Section (b) of FIG. 5 shows a histogram of outcomes for sustained decoder trials following discrete click (light) and sustained click (dark) calibration. Section (c) of FIG. 5 shows click locations (rotated to align across target directions) during transient decoder 130 trials trained using discrete click calibration (506) or sustained click calibration (508). Section (d) of FIG. 5 shows a histogram of outcomes for transient decoder 130 trials.

During the point-and-click task, the sustained click decoder was only effective when trained on the discrete click calibration task (502). Almost all trials of this type fell into two categories—success and early click—with roughly equal probability. The relatively low success rate in comparison to previous studies is likely because we only examined the first click on each trial when determining success or failure rather than allowing multiple attempts following an errant first click. When trained on the sustained click calibration task, the sustained decoder failed to provide adequate control, with a high occurrence of early clicks. This indicates that sustained grasp-related neural activity is not easily isolated from translation-related signals during simultaneous control.

Unlike the sustained click decoder, the transient decoder 130 was successful at providing point-and-click functionality regardless of calibration routine (506, 508, section (d)). It did display a higher incidence of "drag out" failures (i.e. failing to unclick before leaving the target). However, this can likely be attributed more to limitations in translation control than to a failure of click control. From the click locations shown in 506 and 508, the "drag out" failures almost exclusively occurred on trials where the participant clicked on the outer edge of the target. Thus, those trials appear to reflect a failure in stabilizing the cursor, and not necessarily a failure in release control.

Figure 6:
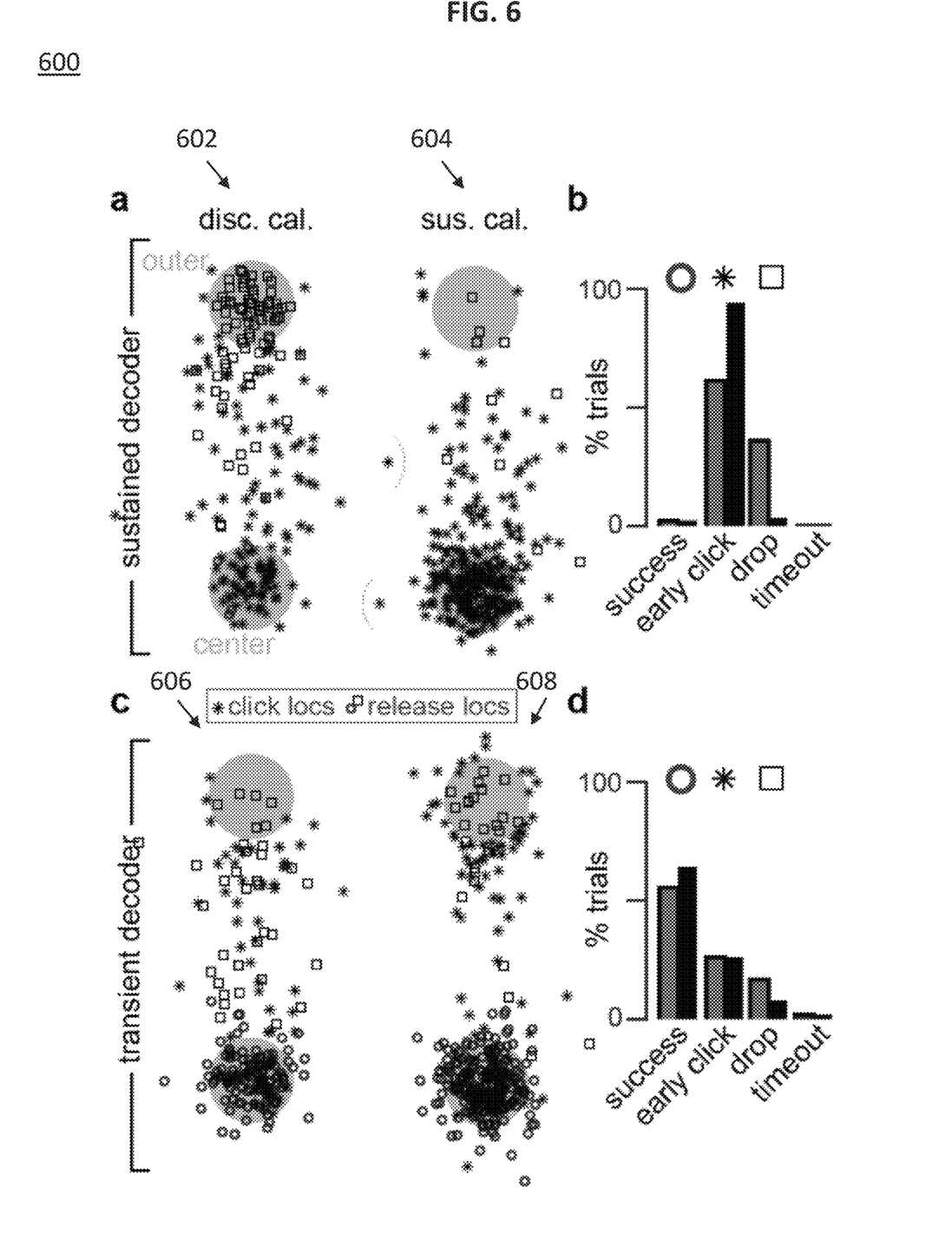
FIG. 6 illustrates results of the click-and-drag task, in accordance with some embodiments.

FIG. 6 illustrates results 600 of the click-and-drag task, in accordance with some embodiments. Click-and-drag performance for P2. Section (a) of FIG. 6 shows key click and release locations (rotated to align across target directions) during sustained decoder trials trained using discrete click calibration (602) or sustained click calibration (604). Open circles represent release locations on successful trials, where the participant successfully dragged the outer target back to the center. Star points or asterisks (*) represent the click locations on failed trials with initial clicks outside of the target. Crosses or 'x's' (x) represent release locations on failed trials in which the participant grabbed the outer target, but released before reaching the center target. Section (b) of FIG. 6 shows histogram of outcomes for sustained decoder trials following discrete click (light) and sustained click (dark) calibration. Section (c) of FIG. 6 shows key click and release locations (rotated to align across target directions) during transient decoder 130 trials trained using discrete click calibration (602) or sustained click calibration (604). Section (d) of FIG. 6 shows histogram of outcomes for transient decoder 130 trials.

The sustained click decoder was unable to provide any meaningful drag functionality, regardless of calibration routine (602, 604, section (b)). However, the types of failures depended on the calibration routine. When trained on discrete click calibration, the participant was able to successfully reach the outer target on a significant number of trials. However, he was unable to maintain click during translation back to the center target, and almost every trial ended with an early drop. This failure to maintain the click is a result of the limitations caused by the calibration routine. The discrete click calibration routine only included interleaved translation and click. Thus, the resulting classifier was not able to generalize to the condition in which translation coincided with click. When trained on the sustained click calibration routine, the sustained click decoder behaved equally poorly, but the failures almost entirely resulted from early click—this failure type corresponds to false positives during grasp classification.

The transient decoder 130 provided high click-and-drag functionality regardless of calibration routine (606, 608, section (d)). As during the point-and-click task, the most common failure was an early click before reaching the target. However, especially for the decoder trained following the sustained click calibration routine (608), the majority of early clicks occurred just outside of the outer target, and thus appear to reflect inadequacies in translation control rather than click control. The decoder trained from sustained click calibration also had a lower incidence of drops (17% vs 8%, section (d)), suggesting slightly better release control. Together, these results indicate that while the performance of a transient decoder 130 approach is largely invariant to the calibration task, a calibration routine involving sustained click (i.e. translation in both clicked and unclicked states) may lower the incidence of both unintentional clicks (section (d) of FIGS. 5-6) and unintentional releases (section (d)).

While certain embodiments have been illustrated and described, it should be understood that changes and modifications can be made therein in accordance with ordinary skill in the art without departing from the technology in its broader aspects as defined in the following claims.

The embodiments, illustratively described herein may suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the claimed technology. Additionally, the phrase "consisting essentially of" will be understood to include those elements specifically recited and those additional elements that do not materially affect the basic and novel characteristics of the claimed technology. The phrase "consisting of" excludes any element not specified.

The present disclosure is not to be limited in terms of the particular embodiments described in this application. Many modifications and variations can be made without departing from its spirit and scope, as will be apparent to those skilled in the art. Functionally equivalent methods and compositions within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, which can of course vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof, inclusive of the endpoints. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member.

All publications, patent applications, issued patents, and other documents referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

Other embodiments are set forth in the following claims.

What is claimed is:

1. A device for processing neural signals, comprising:
   at least one processor configured to:
   receive a plurality of neural signals from a subject, the plurality of neural signals comprising cortical based neural signals;
   detect, from the plurality of neural signals, first neural activity unique to a first defined temporal window corresponding to an onset phase of an intended action of the subject, the first neural activity occurring prior to any physical performance of the intended action;
   detect, from the plurality of neural signals, second neural activity unique to a second defined temporal window, occurring after the first defined temporal window and corresponding to a start of an offset phase of the intended action;
   determine termination of the intended action, the termination of the intended action corresponding to the start of the offset phase; and
   generate at least one output indicative of the intended action, responsive to detecting the first neural activity and the second neural activity.

2. The device of claim 1, wherein the at least one processor is configured to at least one of:
   detect the onset phase by detecting that a probability of a presence of the first neural activity corresponding to the onset phase is at least one of: greater than a first defined value, or greater than a probability of a presence of the second neural activity corresponding to the offset phase; or
   detect the offset phase by detecting that the probability of the second neural activity corresponding to the offset phase is at least one of: greater than a second defined value, or greater than the probability of the presence of the first neural activity corresponding to the onset phase.

3. The device of claim 1, wherein the at least one processor is further configured to:
   reduce the plurality of neural signals to a first subset of neural signals and a second subset of neural signals;
   detect, using the first subset of neural signals, the first neural activity; and
   detect, using the second subset of neural signals, the second neural activity.

4. The device of claim 3, wherein the at least one processor is further configured to perform reduction of the plurality of neural signals using another plurality of neural signals different from the plurality of neural signals.

5. The device of claim 1, wherein the at least one processor is further configured to at least one of:
   shift the first defined temporal window over time to isolate the first neural activity; or
   shift the second defined temporal window over time to isolate the second neural activity.

6. The device of claim 1, wherein:
   the onset phase of the intended action corresponds to one of: a grasp, click, pull, activate, press, push or application of force or pressure; and
   the offset phase of the intended action corresponds to one of: an ungrasp, release, relaxation, unclick, or termination of the force or pressure.

7. The device of claim 1, wherein the intended action corresponds to a grasp and ungrasp action, a click and release action, an activate and release action, a press and release action, a drag and drop action, a pull and release action, or an application of force or pressure sustained over a finite period.

8. A method of a neural signal processing device, comprising:
   receiving a plurality of neural signals from a subject, the plurality of neural signals comprising cortical based neural signals;
   detecting, from the plurality of neural signals, first neural activity unique to a first defined temporal window corresponding to an onset phase of an intended action of the subject, the first neural activity occurring prior to any physical performance of the intended action;
   detecting, from the plurality of neural signals, second neural activity unique to a second defined temporal window, occurring after the first defined temporal window and corresponding to a start of an offset phase of the intended action;
   determining termination of the intended action, the termination of the intended action corresponding to the start of the offset phase; and
   generating at least one output indicative of the intended action, responsive to detecting the first neural activity and the second neural activity.

9. The method of claim 8, further comprising at least one of:
   detecting the onset phase by detecting that a probability of a presence of the first neural activity corresponding to the onset phase is at least one of: greater than a first defined value, or greater than a probability of a presence of the second neural activity corresponding to the offset phase; or
   detecting the offset phase by detecting that the probability of the presence of the second neural activity corresponding to the offset phase is at least one of: greater than a second defined value, or greater than the probability of the presence of the first neural activity corresponding to the onset phase.

10. The method of claim 8, further comprising:
    reducing the plurality of neural signals to a first subset of neural signals and a second subset of neural signals;
    detecting, using the first subset of neural signals, the first neural activity; and
    detecting, using the second subset of neural signals, the second neural activity.

11. The method of claim 10, further comprising training a model to perform reduction of the plurality of neural signals using another plurality of neural signals different from the plurality of neural signals.

12. The method of claim 8, further comprising at least one of:
    shifting the first defined temporal window over time to isolate the first neural activity; or
    shifting the second defined temporal window over time to isolate the second neural activity.

13. The method of claim 8, wherein:
the onset phase of the intended action corresponds to one of: a grasp, click, pull, activate, press, push or application of force or pressure; and
the offset phase of the intended action corresponds to one of: an ungrasp, release, relaxation, unclick, or termination of the force or pressure.

14. The method of claim 8, wherein the intended action corresponds to a grasp and ungrasp action, a click and release action, an activate and release action, a press and release action, a drag and drop action, a pull and release action, or an application of force or pressure sustained over a finite period.

15. A non-transitory computer readable storage medium comprising instructions stored thereon that, when executed by at least one processor, cause the at least one processor to:
receive a plurality of neural signals from a subject, the plurality of neural signals comprising cortical based neural signals;
detect, from the plurality of neural signals, first neural activity unique to a first defined temporal window corresponding to an onset phase of an intended action of the subject, the first neural activity occurring prior to any physical performance of the intended action;
detect, from the plurality of neural signals, second neural activity unique to a second defined temporal window, occurring after the first defined temporal window and corresponding to a start of an offset phase of the intended action;
determine termination of the intended action, the termination of the intended action corresponding to the start of the offset phase; and
generate at least one output indicative of the intended action, responsive to detecting the first neural activity and the second neural activity.

16. The non-transitory computer readable storage medium of claim 15, further comprising instructions that, when executed by the at least one processor, cause the at least one processor to:
detect the onset phase by detecting that a probability of a presence of the first neural activity corresponding to the onset phase is at least one of: greater than a first defined value, or greater than a probability of a presence of the second neural activity corresponding to the offset phase; or
detect the offset phase by detecting that the probability of the presence of the second neural activity corresponding to the offset phase is at least one of: greater than a second defined value, or greater than the probability of the presence of the first neural activity corresponding to the onset phase.

17. The non-transitory computer readable storage medium of claim 15, further comprising instructions that, when executed by the at least one processor, cause the at least one processor to:
reduce the plurality of neural signals to a first subset of neural signals and a second subset of neural signals;
detect, using the first subset of neural signals, the first neural activity; and
detect, using the second subset of neural signals, the second neural activity.

18. The non-transitory computer readable storage medium of claim 17, further comprising instructions that, when executed by the at least one processor, cause the at least one processor to perform reduction of the plurality of neural signals using another plurality of neural signals different from the plurality of neural signals.

19. The non-transitory computer readable storage medium of claim 15, further comprising instructions that, when executed by the at least one processor, cause the at least one processor to:
shift the first defined temporal window over time to isolate the first neural activity; or
shift the second defined temporal window over time to isolate the second neural activity.

20. The non-transitory computer readable storage medium of claim 15, wherein:
the onset phase of the intended action corresponds to one of: a grasp, click, pull, activate, press, push or application of force or pressure; and
the offset phase of the intended action corresponds to one of: an ungrasp, release, relaxation, unclick, or termination of the force or pressure.

* * * * *